(12) United States Patent
Sanganee et al.

(10) Patent No.: US 7,482,363 B2
(45) Date of Patent: *Jan. 27, 2009

(54) PIPERIDINE DERIVATIVES USEFUL AS MODULATORS OF CHEMOKINE RECEPTOR ACTIVITY

(75) Inventors: Hitesh Sanganee, Loughborough (GB); Brian Springthorpe, Loughborough (GB)

(73) Assignee: AstraZeneca AB (SE)

( * ) Notice: Subject to any disclaimer, the term of this patent is extended or adjusted under 35 U.S.C. 154(b) by 784 days.

This patent is subject to a terminal disclaimer.

(21) Appl. No.: 10/508,332

(22) PCT Filed: Mar. 17, 2003

(86) PCT No.: PCT/SE03/00442

§ 371 (c)(1),
(2), (4) Date: Sep. 17, 2004

(87) PCT Pub. No.: WO03/078421

PCT Pub. Date: Sep. 25, 2003

(65) Prior Publication Data

US 2005/0182094 A1 Aug. 18, 2005

(30) Foreign Application Priority Data

Mar. 19, 2002 (SE) .................... 0200843

(51) Int. Cl.
*A61K 31/4468* (2006.01)
*C07D 211/14* (2006.01)
(52) U.S. Cl. ............... 514/316; 546/188; 546/189; 546/191
(58) Field of Classification Search ............... 514/316; 546/188, 189, 191
See application file for complete search history.

(56) References Cited

U.S. PATENT DOCUMENTS

| | | | |
|---|---|---|---|
| 4,588,722 A | 5/1986 | Janssens et al. |
| 4,695,575 A | 9/1987 | Janssens et al. |
| 5,883,096 A | 3/1999 | Lowe et al. |
| 5,889,006 A | 3/1999 | Lowe et al. |
| 5,952,349 A | 9/1999 | Asberom et al. |
| 5,977,138 A | 11/1999 | Wang et al. |
| 6,066,636 A | 5/2000 | Kozlowski et al. |
| 6,294,554 B1 | 9/2001 | Clader et al. |
| 6,387,930 B1 | 5/2002 | Baroudy et al. |
| 6,440,440 B1 | 8/2002 | Meerpoel et al. |
| 6,525,070 B2 | 2/2003 | Rigby et al. |
| 6,759,411 B2 | 7/2004 | Ko et al. |
| 6,903,115 B2 | 6/2005 | Rigby et al. |
| 7,179,922 B2 | 2/2007 | Lawrence et al. |
| 7,186,718 B2 | 3/2007 | Gustafsson et al. |
| 7,238,691 B2 | 7/2007 | Sanganee et al. |
| 7,238,811 B2 | 7/2007 | Lawrence et al. |
| 7,265,227 B2 | 9/2007 | Evans et al. |
| 7,307,090 B2 | 12/2007 | Evans et al. |
| 2005/0176708 A1 | 8/2005 | Luckhurst et al. |
| 2006/0040984 A1 | 2/2006 | Luckhurst et al. |
| 2006/0264463 A1 | 11/2006 | Luckhurst et al. |
| 2006/0281726 A1 | 12/2006 | Luckhurst et al. |
| 2007/0032523 A1 | 2/2007 | Caffrey et al. |
| 2007/0179297 A1 | 8/2007 | Lawrence et al. |

FOREIGN PATENT DOCUMENTS

| | | |
|---|---|---|
| EP | 0 099 139 | 1/1984 |
| EP | 0 121 972 | 10/1984 |
| EP | 0 145 037 | 6/1985 |
| EP | 0 151 824 | 8/1985 |
| EP | 0 151 826 | 8/1985 |
| EP | 1 076 055 | 2/2001 |
| EP | 1 362 857 | 11/2003 |
| EP | 1 389 616 | 2/2004 |
| GB | 1250719 | 10/1971 |
| GB | 2 373 186 | 9/2002 |
| WO | WO 93/10091 A2 | 5/1993 |
| WO | WO 95/08535 | 3/1995 |
| WO | WO 96/26196 | 8/1996 |
| WO | WO 96/34857 | 11/1996 |
| WO | WO 96/41631 A1 | 12/1996 |
| WO | WO 97/24324 | 7/1997 |
| WO | WO 98/01425 | 1/1998 |
| WO | WO 98/05291 | 2/1998 |
| WO | WO 98/05292 | 2/1998 |

(Continued)

OTHER PUBLICATIONS

STN International, File CAPLUS, CAPLUS accession No. 1988:630911, Document No. 109:230911, Lehmann, Jochen et al: "Lactones. XVIII. Synthesis of lactone-bridged 1,1-diarylpropanamines"; & Arch. Pharm. (Weinheim, Ger.) (1988), 321(8), 443-5.

(Continued)

*Primary Examiner*—Rei-Tsang Shiao
*Assistant Examiner*—Joseph R Kosack
(74) *Attorney, Agent, or Firm*—Fish & Richardson P.C.

(57) ABSTRACT

The present invention provides a compound of formula (I), wherein the variables are defined herein; to a process for preparing such a compound; and to the use of such a compound in the treatment of a chemokine (such as CCR3) or H1 mediated disease state.

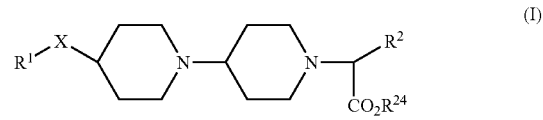

7 Claims, No Drawings

FOREIGN PATENT DOCUMENTS

| | | |
|---|---|---|
| WO | WO 98/06697 | 2/1998 |
| WO | WO 98/11128 | 3/1998 |
| WO | WO 99/04794 | 2/1999 |
| WO | WO 99/37304 | 7/1999 |
| WO | WO 99/38514 | 8/1999 |
| WO | WO 99/51578 | 10/1999 |
| WO | WO 99/55324 | 11/1999 |
| WO | WO 00/00488 | 1/2000 |
| WO | WO 00/12478 | 3/2000 |
| WO | WO 00/32590 | 6/2000 |
| WO | WO 00/35877 A1 | 6/2000 |
| WO | WO 00/66559 A1 | 11/2000 |
| WO | WO 01/02381 | 1/2001 |
| WO | WO 01/07436 | 2/2001 |
| WO | WO 01/29066 A2 | 4/2001 |
| WO | WO 01/77101 A1 | 10/2001 |
| WO | WO 01/92227 | 12/2001 |
| WO | WO 02/18335 | 3/2002 |
| WO | WO 02/20484 | 3/2002 |
| WO | WO 02/066460 | 8/2002 |
| WO | WO 02/072570 | 9/2002 |
| WO | WO 02/079190 | 10/2002 |
| WO | WO 02/079194 | 10/2002 |
| WO | WO 02/081449 | 10/2002 |
| WO | WO 03/004487 | 1/2003 |
| WO | WO 03/018576 | 3/2003 |
| WO | WO 03/020716 | 3/2003 |
| WO | WO 03/022277 | 3/2003 |
| WO | WO 03/024962 | 3/2003 |
| WO | WO 03/078395 | 9/2003 |
| WO | WO 2004/029041 | 4/2004 |
| WO | WO 2004/085423 | 10/2004 |
| WO | WO 2004/087659 | 10/2004 |
| WO | WO 2004/099144 | 11/2004 |
| WO | WO 2004/113323 | 12/2004 |
| WO | WO 2005/097775 | 10/2005 |
| WO | WO 2006/126947 | 11/2006 |
| WO | WO 2006/126948 | 11/2006 |
| WO | WO 2007/011293 | 1/2007 |

OTHER PUBLICATIONS

Allain et al., (2005) STN International, HCAPLUS Database, Columbus, OH, Accession No. 1992:187881, Reg. No. 46817-91-8, citing "Antidepressants and cognition: comparative effects of moclobemide, viloxazine and maprotiline", *Psychopharmacology* 106 (Suppl.).

Cohen et al., *Am. J. Clin. Pathol.* 105:589 (1996).

Hermans et al., "4-Substituted Piperidines. II. Reaction of 1-Benzyl-4-cyano-4-*t*-aminopiperidines with Organometallic Compounds", *J. Med. Chem.* 8(6):851-855 (1965) at p. 852 ("compound 12" in Table I).

Patani and LaVoie, "Bioisosterism: A Rational Approach in Drug Design", *Chem. Rev.* 96:3147-3176 (1996).

Harada et al., "Novel *N*-[1-(1-Substituted 4-Piperidinylmethyl)-4-piperidinyl]benzamides as Potent Colonic Prokinetic Agents", *Bioorganic & Medicinal Chemistry Letters* 12:967-970 (2002).

Hodgson et al., "Chemokines and Drug Discovery", *Drug New Perspect* 17(5):335-338 (2004).

Hoffman et al., "The Preparation of 2-Hydrazinyl Esters in High Optical Purity from 2-Sulfonyloxy Esters", *Tetrahedron Letters* 31(21):2953-2956 (1990).

PIPERIDINE DERIVATIVES USEFUL AS MODULATORS OF CHEMOKINE RECEPTOR ACTIVITY

CROSS-REFERENCE TO RELATED APPLICATIONS

This application is the national phase application under 35 U.S.C. § 371 of PCT International Application No. PCT/SE03/00442, filed Mar. 17, 2003, which claims priority to Swedish Application Serial No. 0200843-1, filed Mar. 19, 2002.

The present invention concerns piperidine derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in WO99/38514, WO99/04794 and WO00/35877.

Histamine is a basic amine, 2-(4-imidazolyl)-ethylamine, and is formed from histidine by histidine decarboxylase. It is found in most tissues of the body, but is present in high concentrations in the lung, skin and in the gastrointestinal tract. At the cellular level inflammatory cells such as mast cells and basophils store large amounts of histamine. It is recognised that the degranulation of mast cells and basophils and the subsequent release of histamine is a fundamental mechanism responsible for the clinical manifestation of an allergic process. Histamine produces its actions by an effect on specific histamine G-protein coupled receptors, which are of three main types, H1, H2 and H3. Histamine H1 antagonists comprise the largest class of medications used in the treatment of patients with allergic disorders, such as rhinitis and urticaria. H1 antagonists are useful in controlling the allergic response by for example blocking the action of histamine on post-capillary venule smooth muscle, resulting in decreased vascular permeability, exudation and oedema The antagonists also produce blockade of the actions of histamine on the H1 receptors on c-type nociceptive nerve fibres, resulting in decreased itching and sneezing.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important rôle in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C—X—C, or α) and Cys-Cys (C—C, or β) families. These are distinguished on the basis of a single amino acid insertion between the NH-proximal pair of cysteine residues and sequence similarity.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Viral infections are known to cause lung inflammation. It has been shown experimentally that the common cold increases mucosal output of eotaxin in the airways. Instillation of eotaxin into the nose can mimic some of the signs and symptoms of a common cold. (See, Greiff L et al Allergy (1999) 54(11) 1204-8 [Experimental common cold increase mucosal output of eotaxin in atopic individuals] and Kawaguchi M et al Int. Arch. Allergy Immunol. (2000) 122 S1 44 [Expression of eotaxin by normal airway epithelial cells after virus A infection].)

The present invention provides a compound of formula (I):

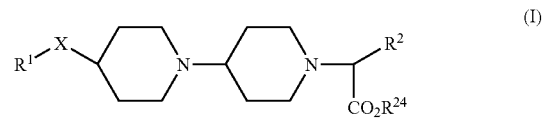

(I)

wherein:

X is $CH_2$, C(O), O, S, S(O), $S(O)_2$ or $NR^3$;

$R^1$ is hydrogen, $C_{1-6}$ alkyl, aryl or heterocyclyl;

$R^2$ is $C_{3-7}$ cycloalkyl {optionally substituted by $C_{1-4}$ alkyl, aryl or oxo}, $C_{3-7}$ cycloalkenyl {optionally substituted by oxo, $C_{1-6}$ alkyl or aryl}, aryl or heterocyclyl;

wherein the foregoing aryl and heterocyclyl moieties are optionally substituted by: halogen, cyano, nitro, hydroxy, oxo, $S(O)_p R^4$, $OC(O)NR^5R^6$, $NR^7R^8$, $NR^9C(O)R^{10}$, $NR^{11}C(O)NR^{12}R^{13}$, $S(O)_2NR^{14}R^{15}$, $NR^{16}S(O)_2R^{17}$, $C(O)NR^{18}R^{19}$, $C(O)R^{20}$, $CO_2R^{21}$, $NR^{22}CO_2R^{23}$, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkoxy($C_{1-6}$)alkoxy, $C_{1-6}$ alkylthio, $C_{1-6}$ haloalkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, phenyl, phenyl($C_{1-4}$)alkyl, phenoxy, phenylthio, phenyl($C_{1-4}$)alkoxy, heterocyclyl, heterocyclyl($C_{1-4}$)alkyl, heterocyclyloxy or heterocyclyl($C_{1-4}$)alkoxy; wherein any of the immediately foregoing phenyl and heterocyclyl moieties are optionally substituted with halogen, hydroxy, nitro, $S(O)_q(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$;

p and q are, independently, 0, 1 or 2;

$R^3$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, $R^{20}$, $R^{21}$ and $R^{22}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^5$ and $R^6$ below), $S(O)_2(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl$)_2$ (and these alkyl groups may join to form a ring as described for $R^5$ and $R^6$ below), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^5$ and $R^6$ below), cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);

alternatively $NR^5R^6$, $NR^7R^8$, $NR^{12}R^{13}$, $NR^{14}R^{15}$, $NR^{18}R^{19}$, may, independently, form a 4-7 membered heterocyclic ring, azetidine, pyrrolidine, piperidine, azepine, 1,4-morpholine or 1,4-piperazine, the latter optionally substituted by $C_{1-4}$alkyl on the distal nitrogen;

$R^4$, $R^{17}$ and $R^{23}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl$)_2$ (and these alkyl groups may join to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl$)_2$ (and these alkyl groups may join to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C)_{1-4}$ alkyl), $CF_3$ or $OCF_3$);

$R^{24}$ is hydrogen, $C_{1-6}$ alkyl or benzyl;

or an N-oxide thereof; or a pharmaceutically acceptable salt thereof; or a solvate thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, dihydrochloride, hydrobromide, phosphate, acetate, diacetate, fumarate, maleate, tartrate, citrate, oxalate, methanesulphonate or p-toluenesulphonate. Another example of an addition salt is sulphate. Salts also include metal salts, such as a sodium, potassium, magnesium or calcium salt.

The compounds of the invention may exist as solvates (such as hydrates) and the present invention covers all such solvates.

Halogen includes fluorine, chlorine, bromine and iodine. Halogen is, for example, fluorine or chlorine.

Alkyl groups and moieties are straight or branched chain and are, for example, methyl, ethyl, n-propyl, iso-propyl or tert-butyl.

Alkenyl groups are, for example, vinyl or allyl.

Cycloalkyl is mono-, bi or tricyclic and is, for example, cyclopropyl, cyclopentyl, cyclohexyl, norbornyl or camphoryl. The cycloalkyl ring is optionally fused to a benzene ring (for example forming a bicyclo[4.2.0]octa-1,3,5-trienyl or indanyl ring system).

Cycloalkenyl is, for example, monocyclic and is, for example, cyclopentenyl or cyclohexenyl.

Aryl is, for example, phenyl or naphthyl.

Heterocyclyl is an aromatic or non-aromatic 5 or 6 membered ring, optionally fused to one or more other rings, comprising at least one heteroatom selected from the group comprising nitrogen, oxygen and sulphur; or an N-oxide thereof, or an S-oxide or S-dioxide thereof. Heterocyclyl is, for example, furyl, thienyl (also known as thiophenyl), pyrrolyl, 2,5-dihydropyrrolyl, thiazolyl, pyrazolyl, oxazolyl, isoxazolyl, imidazolyl, piperidinyl, morpholinyl, pyridinyl (for example in 6-oxo-1,6-dihydro-pyridinyl), pyrimidinyl, indolyl, 2,3-dihydroindolyl, benzo[b]furyl (also known as benzofuryl), benz[b]thienyl (also known as benzthienyl or benzthiophenyl), 2,3-dihydrobenz[b]thienyl (for example in 1-dioxo-2,3-dihydrobenz[b]thienyl), indazolyl, benzimidazolyl, benztriazolyl, benzoxazolyl, benzthiazolyl (for example in 1H-benzthiazol-2-one-yl), 2,3-dihydrobenzthiazolyl (for example in 2,3-dihydrobenzthiazol-2-one-yl), 1,2,3-benzothiadiazolyl, an imidazopyridinyl (such as imidazo[1,2a]pyridinyl), thieno[3,2-b]pyridin-6-yl 1,2,3-benzoxadiazolyl, benzo[1,2,3]thiadiazolyl, 2,1,3-benzothiadiazolyl, benzofurazan (also known as 2,1,3-benzoxadiazolyl), quinoxalinyl, dihydro-1-benzopyryliumyl (for example in a coumarinyl or a chromonyl), 3,4-dihydro-1H-2,1-benzothiazinyl (for example in 2-dioxo-3,4-dihydro-1H-2,1-benzothiazinyl), a pyrazolopyridine (for example 1H-pyrazolo[3,4-b]pyridinyl), a purine (for example in 3,7-dihydro-purin-2,6-dione-8-yl), quinolinyl, isoquinolinyl (for example in 2H-isoquinolin-1-one-yl), a naphthyridinyl (for example [1,6]naphthyridinyl or [1,8]naphthyridinyl or in 1H-[1,8]naphthyridin4-one-yl), a benzothiazinyl (for example in 4H-benzo[1,4]thiazin-3-one-yl), benzo[d]imidazo[2,1-b]thiazol-2-yl or dibenzothiophenyl (also known as dibenzothienyl); or an N-oxide thereof, or an S-oxide or S-dioxide thereof. Heterocyclyl also includes isothiazolyl.

An N-oxide of a compound of formula (I) is, for example, a 1-oxy-[1,4']bipiperidinyl-1'-yl compound.

In one particular aspect the invention provides a compound of formula (I) wherein X is O.

In a further aspect $R^{24}$ is hydrogen.

In another aspect $R^1$ is phenyl optionally substituted with fluorine, chlorine, $C_{1-4}$ alkyl (for example methyl) or $C_{1-4}$ alkoxy (for example methoxy).

In yet another aspect $R^1$ is phenyl optionally substituted (for example with one, two or three) with fluorine, chlorine, $C_{1-4}$ alkyl (for example methyl) or $C_{1-4}$ alkoxy (for example methoxy). In a further aspect $R^1$ is phenyl optionally substituted (for example with one, two or three) with fluorine, chlorine or $C_{1-4}$ alkyl (for example methyl). In a still further aspect $R^1$ is phenyl substituted by one, two or three of fluorine, chlorine, methyl or methoxy. For example $R^1$ is 3,4-dichlorophenyl, 2,4-dichloro-3-methylphenyl, 3,4-dichloro-2-methylphenyl, 2,4-dichlorophenyl, 4-chloro-2-methylphenyl or 2-chloro4-fluorophenyl.

In a still further aspect $R^1$ is phenyl optionally substituted (for example independently di-substituted) with halogen (for example chlorine) or $C_{1-4}$ alkyl (for example methyl).

In a further aspect $R^2$ is unsubstituted phenyl, mono-substituted phenyl or mono-substituted heterocyclyl, the substituents being chosen from those described above.

In a still further aspect $R^2$ is oxo substituted heterocyclyl, said heterocyclyl optionally further substituted with one or more substituents chosen from those described above.

In another aspect $R^2$ is phenyl or heterocyclyl, either of which is optionally substituted by: halo, hydroxy, nitro, cyano, amino, $C_{1-4}$ alkyl (itself optionally substituted by $S(O)_2(C_{1-4}$ alkyl) or $S(O)_2$phenyl), $C_{1-4}$ alkoxy, $S(O)_pR^4$ (wherein p is 0, 1 or 2 (for example 2)), $C(O)NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl)$_2$; and $R^4$ is $C_{1-4}$ alkyl, $C_{1-4}$ hydroxyalkyl, $C_{3-7}$ cycloalkyl or $C_{3-7}$ cycloalkyl($C_{1-4}$ alkyl)(such as cyclopropylmethyl).

In a further aspect $R^2$ is phenyl mono-substituted by halo, hydroxy, nitro, cyano, amino, $C_{1-4}$ alkyl (itself optionally substituted by $S(O)_2(C_{1-4}$ alkyl) or $S(O)_2$phenyl), $C_{1-4}$ alkoxy, $S(O)_pR^4$ (wherein p is 0, 1 or 2 (for example 2)), $C(O)NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl)$_2$; and $R^4$ is $C_{1-4}$ alkyl, $C_{1-4}$ hydroxyalkyl, $C_{3-7}$ cycloalkyl or $C_{3-7}$ cycloalkyl($C_{1-4}$ alkyl) (such as cyclopropylmethyl).

In yet another aspect $R^2$ is phenyl (optionally substituted by $C_{1-6}$ alkyl (itself optionally mono-substituted by hydroxy), $C_{1-6}$ alkoxy or phenyl), naphthylenyl (optionally substituted by $C_{1-4}$ alkoxy) or heterocyclyl.

Heterocyclyl is, for example, thienyl, furanyl, benzofuranyl or benzo[b]thienyl. In a further aspect of the invention heterocyclyl is optionally substituted by halogen, $C_{1-4}$ alkyl or $C_{1-4}$ alkoxy.

In a further aspect the present invention provides a compound of formula (I) wherein X is O; $R^1$ is phenyl optionally substituted by halogen (for example chlorine) or $C_{1-4}$ alkyl (for example methyl); and $R^2$ is as defined above.

A compound of formula (I) can be prepared by coupling a compound of formula (II):

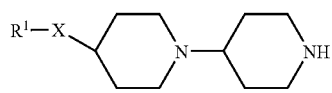

(II)

with a compound of formula (III):

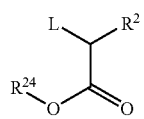

(III)

wherein L is a suitable leaving group (such as can be halogen (such as chloro) or $C_{1-6}$ alkylsulfonyl) and the coupling can be carried out in a suitable solvent (such as water).

Alternatively, a compound of formula (I) can be prepared by reductive amination of a compound (II) with an ester (such as a $C_{1-6}$ alkyl ester or a benzyl ester) of a compound of formula (IIIa):

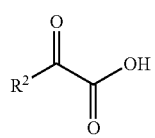

(IIIa)

in the presence of $NaBH(OAc)_3$ and acetic acid, optionally followed by removal of the ester group.

Alternatively, a compound of formula (I) where $R^{24}$ represents H can be prepared by a three component coupling of a compound of formula (II) with compounds of formula (IIIb) and (IIIc):

(IIIb)

(IIIc)

A compound of formula (II) can be prepared by deprotecting a compound of formula (IV):

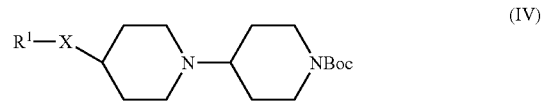

(IV)

for example using trifluoroacetic acid in a suitable solvent (such as dichloromethane) or using a source of hydrogen chloride in a suitable solvent (such as dioxane).

A compound of formula (IV), wherein X is O, can be prepared by reacting a compound of formula (V):

(V)

with a compound of formula (VI):

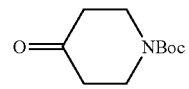

(VI)

in the presence of $NaBH(OAc)_3$ and acetic acid.

A compound of formula (IV), wherein X is CO or $CH_2$, can be prepared by oxidising or reducing a compound of formula (VII):

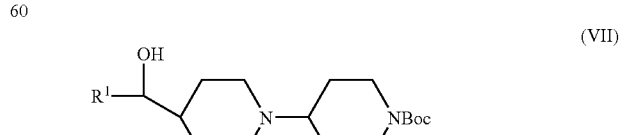

(VII)

A compound of formula (VII) can be prepared by reacting a compound of formula (VIII):

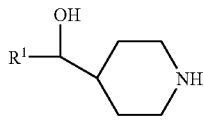
(VIII)

with a compound of formula (VI) in the presence of NaBH(OAc)$_3$ and acetic acid. A compound of formula (VIII) can be prepared by reduction of a compound of formula (IX):

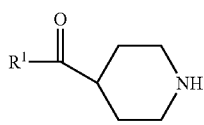
(IX)

A compound of formula (I) wherein X is NR$^3$ can be prepared by reacting a compound of formula (X):

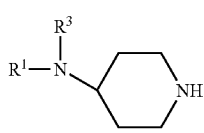
(X)

with a compound of formula (XI):

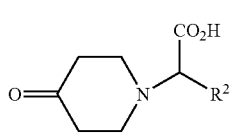
(XI)

in the presence of NaBH(OAc)$_3$ and acetic acid. A compound of formula (X) can be prepared by reacting NHR$^1$R$^3$ with a compound of formula (XII):

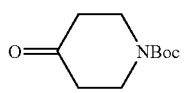
(XII)

in the presence of NaBH(OAc)$_3$ and acetic acid and then deprotecting the piperidine nitrogen {for example using trifluoroacetic acid in a suitable solvent (such as dichloromethane) or using a source of hydrogen chloride in a suitable solvent (such as dioxane)}.

Compounds (IV) where X is O and R$^1$ represents aryl or heterocyclyl may be prepared from a compound of formula (XV):

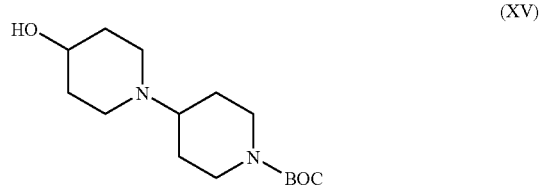
(XV)

and a compound of formula (XVI):

(XVI)

for example using potassium t-butoxide in N-methylpyrrolidinone, for example at 60° C.

Compounds of formula (I) where R$^{24}$ is hydrogen may be converted to compounds of formula (I) where R$^{24}$ is not hydrogen by standard esterifcation methods well known in the art.

Compounds of formula (I) where R$^{24}$ is not hydrogen may be converted to compounds of formula (I) where R$^{24}$ is hydrogen by standard ester hydrolysis methods well known in the art.

The preparation of various intermediates can be found in WO00/66559 and WO01/77101; alternatively they can be prepared by using or adapting literature methods.

Further compounds of formula (I) can be prepared by adaptation of: the routes described above, methods described in the art or the Examples recited below.

Compounds of formula (V), (VI), (IX), (XI), (XII), (XV) and (XVI) can be prepared by using or adapting methods described in the art.

In another aspect the present invention provides processes for the preparation of compounds of formula (I).

The compounds of formula (I) have activity as pharmaceuticals, in particular as modulators of chemokine receptor (for example CCR3) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

Examples of these conditions are:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;
(3) (skin and eyes) psoriasis, atopic dermatitis, contact dermatitis or other eczmatous dermitides, seborrhoetic dermatitis, lichen planus, phemphigus, bullous phemphigus, epidermolysis bullosa, urticaria, angiodermas, vasculitides erythemas, cutaneous eosinophilias, uveitis, alopecia areata, corneal ulcer or vernal conjunctivitis;
(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);
(5) (Allograft rejection) acute and chronic following, for example, transplantation of kidney, heart, liver, lung, bone marrow, skin or cornea; or chronic graft versus host disease; and/or
(6) (other tissues or diseases) Alzheimer's disease, multiple sclerosis, atherosclerosis, Acquired Immunodeficiency Syndrome (AIDS), lupus disorders (such as lupus erythematosus or systemic lupus), erythematosus, Hashimoto's thyroiditis, myasthenia gravis; type I diabetes, nephrotic syndrome, eosinophilia fascitis, hyper IgE syndrome, leprosy (such as lepromatous leprosy), peridontal disease, Sezary syndrome, idiopathic thrombocytopenia pupura or disorders of the menstrual cycle.

The compounds of formula (I) or a pharmaceutically acceptable salt thereof or a solvate thereof, are also H1 antagonists (and can, therefore, be used in the treatment of allergic disorders); and may also be used to control a sign and/or symptom of what is commonly referred to as a cold (for example a sign and/or symptom of a common cold or influenza or other associated respiratory virus infection).

According to a further feature of the present invention there is provided a method for treating a chemokine mediated disease state (for example a CCR3 mediated disease state) in a mammal, such as man, suffering from, or at risk of, said disease state, which comprises administering to a mammal in need of such treatment a therapeutically effective amount of a compound of the formula (I) or a pharmaceutically acceptable salt thereof or a solvate thereof.

According to another feature of the present invention there is provided a method for antagonising H1 in a mammal, such as man, suffering from, or at risk of, an H1 mediated disease state, which comprises administering to a mammal in need of such treatment a therapeutically effective amount of a compound of the formula (I) or a pharmaceutically acceptable salt thereof or a solvate thereof.

According to yet another feature of the present invention there is provided a method for treating a sign and/or symptom of what is commonly referred to as a cold in a mammal, such as man, suffering from, or at risk of, said disease state, which comprises administering to a mammal in need of such treatment a therapeutically effective amount of a compound of the formula (I) or a pharmaceutically acceptable salt thereof or a solvate thereof.

The invention also provides a compound of the formula (I), or a pharmaceutically acceptable salt thereof or a solvate thereof, for use in therapy.

In another aspect the invention provides the use of a compound of formula (I), or a pharmaceutically acceptable salt thereof or a solvate thereof, in the manufacture of a medicament for use in therapy (for example modulating chemokine receptor activity (for example CCR3 receptor activity), antagonising H1 or treating a sign and/or symptom of what is commonly referred to as a cold).

The invention further provides the use of a compound of formula (I), or a pharmaceutically acceptable salt thereof, in the manufacture of a medicament for use in the treatment of:
(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;
(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;
(3) (skin and eyes) psoriasis, atopic dermatitis, contact dermatitis or other eczmatous dermitides, seborrhoetic dermatitis, lichen planus, phemphigus, bullous phemphigus, epidermolysis bullosa, urticaria, angiodermas, vasculitides erythemas, cutaneous eosinophilias, uveitis, alopecia areata, corneal ulcer or vernal conjunctivitis;
(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);
(5) (Allograft rejection) acute and chronic following, for example, transplantation of kidney, heart, liver, lung, bone marrow, skin or cornea; or chronic graft versus host disease; and/or
(6) (other tissues or diseases) Alzheimer's disease, multiple sclerosis, atherosclerosis, Acquired Immunodeficiency Syndrome (AIDS), lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle;

in a mammal (for example man).

In a further aspect the invention provides a compound of formula (I), or a pharmaceutically acceptable salt thereof, for use in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis}.

In a still further aspect a compound of formula (I), or a pharmaceutically acceptable salt thereof, is useful in the treatment of asthma.

The present invention also provides a the use of a compound of formula (I), or a pharmaceutically acceptable salt thereof, in the manufacture of a medicament for use in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis}.

In order to use a compound of the invention, or a pharmaceutically acceptable salt thereof or solvate thereof, for the therapeutic treatment of a mammal, such as man, said ingredient is normally formulated in accordance with standard pharmaceutical practice as a pharmaceutical composition. Therefore in another aspect the present invention provides a pharmaceutical composition which comprises a compound of the formula (I), or a pharmaceutically acceptable salt thereof or a solvate thereof (active ingredient), and a pharmaceutically acceptable adjuvant, diluent or carrier.

In a further aspect the present invention provides a process for the preparation of said composition which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art. A suitable pharmaceutical composition of this invention is one suitable for oral administration in unit dosage form, for example a tablet or capsule which contains between 0.1 mg and 1 g of active ingredient Each patient may receive, for example, a dose of 0.01 $mgkg^{-1}$ to 100 $mgkg^{-1}$, for example in the range of 0.1 $mgkg^{-1}$ to 20 $mgkg^{-1}$, of the active ingredient administered, for example, 1 to 4 times per day.

The invention will now be illustrated by the following non-limiting examples in which, unless stated otherwise:
(i) when given, $^1$H NMR data is quoted and is in the form of delta values for major diagnostic protons, given in parts per million (ppm) relative to tetramethylsilane (TMS) as an internal standard, determined at 300 MHz or 400 MHz using perdeuterio DMSO-D6 ($CD_3SOCD_3$) or $CDCl_3$ as the solvent unless otherwise stated;
(ii) mass spectra (MS) were run with an electron energy of 70 electron volts in the chemical ionisation (CI) mode using a direct exposure probe; where indicated ionisation was effected by electron impact (EI) or fast atom bombardment (FAB); where values for m/z are given, generally only ions which indicate the parent mass are reported, and unless otherwise stated the mass ion quoted is the positive mass ion—$(M+H)^+$;
(iii) the title and sub-title compounds of the examples and methods were named using the index name program from Advanced Chemistry Development Inc;
(iv) unless stated otherwise, reverse phase HPLC was conducted using a Symmetry™, NovaPak™ or Xerra™ reverse phase silica column; and
(v) the following abbreviations are used:

| Boc or BOC | tert-butoxycarbonyl | DMSO | dimethylsulfoxide |
| HPLC | high pressure liquid chromatography | aq | aqueous |

EXAMPLE 1

This Example illustrates the preparation of 4-(3,4-dichlorophenoxy)-α-phenyl-[1,4'-bipiperidine]-1'-acetic acid.

To a solution of 4-(3,4-dichlorophenoxy)-1,4'-bipiperidine (WO 01/77101) (0.500 g) in water (5 ml) was added bromo(phenyl)acetic acid (0.348 g) and the reaction was left to stir for 16 hrs. Evaporation of solvent and purification using reverse phase HPLC (with a gradient eluent system of 5% MeCN/$NH_4OAc_{(aq)}$ (0.1%) to 95% MeCN/$NH_4OAc_{(aq)}$ (0.1%) gave the title compound as a solid (0.049 g).

MS: APCI(–ve): 461 (M—H)$^-$ $^1$H NMR ($CDCl_3$) δ 1.80-2.05 (6H, m), 2.33-2.78 (5H, m), 3.25-3.56 (7H, m), 4.23-4.26 (2H, m), 6.69 (1H, dd), 6.93 (1H, d), 7.28-7.36 (4H, m), 7.52-7.55 (2H, m).

EXAMPLE 2

This Example illustrates the preparation of 4-(3,4-dichlorophenoxy)-α-(2, 6-dimethoxyphenyl)-[1,4'-bipiperidine]-1'-acetic acid.

To a solution of 4-(3,4-dichlorophenoxy)-1,4'-bipiperidine (0.500 g) in ethanol (3 ml) was added 2,6-dimethoxyphenylboronic acid (0.275 g) and oxoacetic acid (0.1 ml). The mixture was heated to 80° C. for 5 minutes using microwaves at 50 Watts. The solvent was removed by evaporation. Purification using reverse phase HPLC (with a gradient eluent system of 5% MeCN/$NH_{3(aq)}$ (0.2%) to 95% MeCN/$NH_{3(aq)}$ (0.2%) gave the title compound (0.210 g).

MS: ES(+ve): 523 (M+H)$^+$ $^1$H NMR ($CDCl_3$) δ 1.75-1.77 (2H, m), 1.89-1.97 (5H, m), 2.04-2.10 (1H, m), 2.39-2.43 (4H, m), 2.73-2.75 (2H, m), 2.84-2.90 (1H, m), 3.48-3.53 (2H, m), 3.84 (6H, s), 4.20-4.26 (1H, m), 5.00 (1H, s), 6.59-6.61 (2H, m), 6.71-6.74 (1H, m), 6.96-6.97 (1H, m), 7.27-7.34 (2H, m).

EXAMPLE 3

This Example illustrates the preparation of 4-(4-chloro-2-methylphenoxy)-α-phenyl-[1,4'-bipiperidine]-1'-acetic acid.

To a solution of 4-(4-chloro-2-methylphenoxy)-1,4'-bipiperidine (0.540 g)(WO 01/77101) in acetonitrile (5 ml) was added phenylboronic acid (0.212 g) and oxoacetic acid (0.1 ml). The mixture was heated to 100° C. for 4 minutes using microwaves at 50 Watts. The crude reaction was put onto an Oasis® MCX cartridge (Waters Chromotography) in MeOH and the cartridge washed with MeOH followed by elution with 20%/$NH_{3(aq)}$/MeOH. Evaporation of solvent and further purification by reverse phase HPLC (with a gradient eluent system of 5% MeCN/$NH_{3(aq)}$ (0.2%) to 95% MeCN/$NH_{3(aq)}$ (0.2%) gave the title compound (0.052 g).

MS: APCI(+ve): 443 (M+H)$^+$ $^1$H NMR ($CD_3OD$) d 1.84-2.11 (8H, m), 2.18 (3H, s), 2.69-3.01 (8H, m), 3.72 (1H, s), 4.27 (1H, s), 4.42-4.47 (1H, m), 6.88 (1H, d), 7.07-7.12 (2H, m), 7.39-7.43 (3H, m), 7.54-7.57 (2H, m).

EXAMPLE 4

This Example illustrates the preparation of methyl 4-(3,4-dichlorophenoxy)-α-phenyl-[1,4'-bipiperidine]-1'-acetate 4-(3,4-Dichlorophenoxy)-1,4'-bipiperidine (0.20 g) and methyl-α-bromophenylacetate (0.14 g) were dissolved in acetone (20 mL). Potassium carbonate (0.08 g) was added. The reaction mixture was stirred at room temperature for 16 h, then filtered and purified via RPHPLC (gradient Ammonium acetate/Acetonitrile 75% to 5% aqueous; Symmetry column) to give the title compound (0.09 g).

MS [M+H]$^+$ (ES+) 477

$^1$H NMR δ(CD$_3$OD) 1.46-1.53 (1H, m), 1.56-1.63 (1H, m), 1.66-1.76 (2H, m), 1.77-1.86 (3H, m), 1.89-1.98 (2H, m), 2.04-2.13 (1H, m), 2.29-2.40 (1H, m), 2.48-2.57 (2H, m), 2.64-2.71 (1H, m), 2.78-2.88 (2H, m), 2.94-3.01 (1H, m), 3.56 (3H, s), 3.93 (1H, s), 4.30-4.37 (1H, m), 6.79 (1H, dd), 7.01 (1H, d), 7.22-7.34 (6H, m).

EXAMPLES 5-24

Examples 5-24 are examples of compounds of formula (I) and were prepared by the following general method.

To a solution of 4-(3,4-dichlorophenoxy)-1,4'-bipiperidine (0.004 g) in dimethyl acetamide (0.150 ml) was added appropriate boronic acid (1 molar equivalent in 0.2 ml of dimethylacetamide) and oxoacetic acid (1.5 molar equivalents). The mixture was heated to 80° C. for 5 minutes using microwaves at 300 Watts. Purification using reverse phase HPLC [with a gradient eluent system of 5% MeCN/NH$_{3(aq)}$ (0.2%) to 95% MeCN/NH$_{3(aq)}$ (2.0%)] gave the required product.

| Example | Name | (M + H)$^+$ |
|---|---|---|
| 5 | 4-(3,4-dichlorophenoxy)-α-[3-(hydroxymethyl)phenyl]-[1,4'-bipiperidine]-1'-acetic acid | 493 |
| 6 | 4-(3,4-dichlorophenoxy)-α-(6-methoxy-2-naphthalenyl)-[1,4'-bipiperidine]-1'-acetic acid | 543 |
| 7 | 4-(3,4-dichlorophenoxy)-α-phenyl-[1,4'-bipiperidine]-1'-acetic acid | 463 |
| 8 | 4-(3,4-dichlorophenoxy)-α-(4-methylphenyl)-[1,4'-bipiperidine]-1'-acetic acid | 477 |
| 9 | 4-(3,4-dichlorophenoxy)-α-(2-thienyl)-[1,4'-bipiperidine]-1'-acetic acid | 469 |
| 10 | 4-(3,4-dichlorophenoxy)-α-(3-thienyl)-[1,4'-bipiperidine]-1'-acetic acid | 469 |
| 11 | α-(2-benzofuranyl)-4-(3,4-dichlorophenoxy)-[1,4'-bipiperidine]-1'-acetic acid | 503 |
| 12 | 4-(3,4-dichlorophenoxy)-α-[4-(1,1-dimethylethoxy)phenyl]-[1,4'-bipiperidine]-1'-acetic acid | 536 |
| 13 | 4-(3,4-dichlorophenoxy)-α-(3-methylphenyl)-[1,4'-bipiperidine]-1'-acetic acid | 477 |
| 14 | 4-(3,4-dichlorophenoxy)-α-(1-naphthalenyl)-[1,4'-bipiperidine]-1'-acetic acid | 513 |
| 15 | 4-(3,4-dichlorophenoxy)-α-(2-naphthalenyl)-[1,4'-bipiperidine]-1'-acetic acid | 513 |
| 16 | α-benzo[b]thien-2-yl-4-(3,4-dichlorophenoxy)-[1,4'-bipiperidine]-1'-acetic acid | 519 |
| 17 | α-[1,1'-biphenyl]-3-yl-4-(3,4-dichlorophenoxy)-[1,4'-bipiperidine]-1'-acetic acid | 540 |
| 18 | 4-(3,4-dichlorophenoxy)-α-(2,6-dimethoxyphenyl)-[1,4'-bipiperidine]-1'-acetic acid | 523 |
| 19 | 4-(3,4-dichlorophenoxy)-α-(3,4-dimethoxyphenyl)-[1,4'-bipiperidine]-1'-acetic acid | 523 |
| 20 | 4-(3,4-dichlorophenoxy)-α-(2,4-dimethoxyphenyl)-[1,4'-bipiperidine]-1'-acetic acid | 523 |
| 21 | 4-(3,4-dichlorophenoxy)-α-[3-(1-methylethyl)phenyl]-[1,4'-bipiperidine]-1'-acetic acid | 505 |
| 22 | 4-(3,4-dichlorophenoxy)-α-(3,4,5-trimethoxyphenyl)]-[1,4'-bipiperidine]-1'-acetic acid | 553 |
| 23 | 4-(3,4-dichlorophenoxy)-α-[4-(1,1-dimethylethyl)phenyl]-[1,4'-bipiperidine]-1'-acetic acid | 520 |

EXAMPLE 24

Pharmacological Analysis: Calcium Flux [Ca$^{2+}$]$_i$ assay

Human Eosinophils

Human eosinophils were isolated from EDTA anticoagulated peripheral blood as previously described (Hansel et al., *J. Immunol. Methods*, 1991, 145, 105-110). The cells were resuspended (5×10$^6$ ml$^{-1}$) and loaded with 5 μM FLUO-3/AM+Pluronic F127 2.2 μl/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at 2.5×10$^6$ ml$^{-1}$. The cells were then transferred to 96 well FLIPr plates (Poly-D-Lysine plates from Becton Dickinson pre-incubated with 5 μM fibronectin for two hours) at 25 μl/well. The plate was centrifuged at 200 g for 5 min and the cells were washed twice with LKS (200 μl; room temperature).

A compound of the Examples was pre-dissolved in DMSO and added to a final concentration of 0.1% (v/v) DMSO. Assays were initiated by the addition of an A$_{50}$ concentration of eotaxin and the transient increase in fluo-3 fluorescence (l$_{Ex}$=490 nm and l$_{Em}$=520 nm) monitored using a FLIPR (Fluorometric Imaging Plate Reader, Molecular Devices, Sunnyvale, U.S.A.).

EXAMPLE 25

Human Eosinophil Chemotaxis

Human eosinophils were isolated from EDTA anticoagulated peripheral blood as previously described (Hansel et al., *J. Immunol. Methods*, 1991, 145, 105-110). The cells were resuspended at 10×10$^6$ ml$^{-1}$ in RPMI containing 200 IU/ml penicillin, 200 μg/ml streptomycin sulphate and supplemented with 10% HIFCS, at room temperature.

Eosinophils (700 μl) were pre-incubated for 15 mins at 37° C. with 7 μl of either vehicle or compound (100× required final concentration in 10% DMSO). The chemotaxis plate (ChemoTx, 3 μm pore, Neuroprobe) was loaded by adding 28 μl of a concentration of eotaxin (0.1 to 100 nM) containing a concentration of a compound according to the Examples or solvent to the lower wells of the chemotaxis plate. The filter was then placed over the wells and 25 μl of eosinophil suspension were added to the top of the filter. The plate was incubated for 1 hr at 37° C. in a humidified incubator with a 95% air/5% CO$_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 μl of PBS containing 0.5% Triton x100 followed by two cycles of freeze/thawing. The cell lysate was then added to the supernatant. The number of eosinophils migrating was quantified according to the method of Strath et al., *J. Immunol. Methods,* 1985, 83, 209 by measuring eosinophil peroxidase activity in the supernatant.

Compounds of the Examples were found to be antagonists of the eotaxin mediated human eosinophil chemotaxis.

| Example | % Inhibition (3 nM Human Eotaxin) |
|---------|-----------------------------------|
| 2       | 90                                |
| 3       | 105                               |

EXAMPLE 26

Guinea-Pig Isolated Trachea (See for example, Harrison, R. W. S., Carswell, H. & Young, J. M. (1984) European J. Pharmacol., 106, 405-409.)

Male albino Dunkin-Hartley guinea-pigs (250 g) were killed by cervical dislocation and the whole trachea removed. After clearing the adherent connective tissue, the trachea was cut into six ring segments each three cartilage bands wide and then suspended in 20 ml organ baths containing Krebs-Henseleit solution of the following composition (mM):NaCl 117.6, $NaH_2PO_4$ 0.9, $NaHCO_3$ 25.0, $MgSO_4$ 1.2, KCl 5.4, $CaCl_2$ 2.6 and glucose 11.1. The buffer was maintained at 37° C. and gassed with 5% $CO_2$ in oxygen. Indomethacin (2.8 μM) was added to the Krebs solution to prevent development of smooth muscle tone due to the synthesis of cyclo-oxygenase products. The tracheal rings were suspended between two parallel tungsten wire hooks, one attached to an Ormed beam isometric force transducer and the other to a stationary support in the organ bath. Changes in isometric force were recorded on 2-channel Sekonic flat bed chart recorders.

Experimental Protocols

At the beginning of each experiment a force of 1 g was applied to the tissues and this was reinstated over a 60 minute equilibration period until a steady resting tone was achieved. Subsequently, a cumulative histamine concentration effect (E/[A]) curve was constructed at 0.5 $log_{10}$ unit increments, in each tissue. The tissues were then washed and approximately 30 minutes later, test compound or vehicle (20% DMSO) was added. Following an incubation period of 60 minutes a second E/[A] curve was performed to histamine.

Contraction responses were recorded as a percentage of the first curve maximum.

Data Analysis

Experimental E/[A] curve data were analysed for the purposes of estimating the potencies (p[$A_{50}$] values) of histamine in the absence and presence of the test compound. Affinity (p$A_2$) values of test compounds were subsequently calculated using the following equation:

$$\log(r-1)=\log[B]+pA_2$$

where r=[$A$]$_{50}$ in presence of test compound/[$A$]$_{50}$ in absence of antagonist and [B] is the concentration of test compound. Compounds of the Examples were found to be H1 antagonists.

EXAMPLE 27

Histamine H1 receptor binding activity of compounds of the invention was assessed by competition displacement of 1 nM [3H]-pyrilamine (Amersham, Bucks, Product code TRK 608, specific activity 30 Ci/mmol) to 2 μg membranes prepared from recombinant CHO-K1 cells expressing the human H1 receptor (Euroscreen SA, Brussels, Belgium, product code ES-390-M) in assay buffer (50 mM Tris pH 7.4 containing 2 mM $MgCl_2$, 250 mM sucrose and 100 mM NaCl) for 1 hour at room temperature.

The following compounds of the invention gave inhibition of [3H] pyrilimine binding:

| Example | H1 antagonism pKi |
|---------|-------------------|
| 1       | 7.2               |
| 2       | 6.8               |
| 3       | 7.3               |
| 4       | 7.2               |

The invention claimed is:
1. A compound of formula (I):

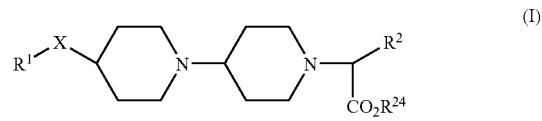

wherein:
X is $CH_2$, C(O), O, S, S(O), $S(O)_2$ or $NR^3$;
$R^1$ is hydrogen, $C_{1-6}$ alkyl, aryl or heterocyclyl;
$R^2$ is $C_{3-7}$ cycloalkyl {optionally substituted by $C_{1-4}$ alkyl, aryl or oxo}, $C_{3-7}$ cycloalkenyl {optionally substituted by oxo, $C_{1-6}$ alkyl or aryl}, aryl or heterocyclyl; wherein the foregoing aryl and heterocyclyl moieties are optionally substituted by: halogen, cyano, nitro, hydroxy, oxo, $S(O)_pR^4$, $OC(O)NR^5R^6$, $NR^7R^8$, $NR^9C(O)R^{10}$, $NR^{11}C(O)NR^{12}R^{13}$, $S(O)_2NR^{14}R^{15}$, $NR^{16}S(O)_2R^{17}$, $C(O)NR^{18}R^{19}$, $C(O)R^{20}$, $CO_2R^{21}$, $NR^{22}CO_2R^{23}$, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkoxy($C_{1-6}$)alkoxy, $C_{1-6}$ alkylthio, $C_{1-6}$ haloalkylthio, $C_{2-6}$ alkenyl, $C_{2-6}$ alkynyl, $C_{3-10}$ cycloalkyl (optionally substituted by $C_{1-4}$ alkyl or oxo), methylenedioxy, difluoromethylenedioxy, phenyl, phenyl($C_{1-4}$)alkyl, phenoxy, phenylthio, phenyl($C_{1-4}$) alkoxy, heterocyclyl, heterocyclyl($C_{1-4}$)alkyl, heterocylyloxy or heterocyclyl($C_{1-4}$)alkoxy; wherein any of the immediately foregoing phenyl and heterocyclyl moieties are optionally substituted with halogen, hydroxy, nitro, $S(O)_q(C_{1-4}alkyl)$, $S(O)_2NH_2$, cyano, $C_{1-4}$ alkyl, $C_{1-4}$ alkoxy, $C(O)NH_2$, $C(O)NH(C_{1-4}$ alkyl), $C(O)N$ ($C_{1-4}$ alkyl)$_2$ (and these alkyl groups optionally being joined to form a ring as described for $R^5$ and $R^6$ below), $CO_2H$, $CO_2(C_{1-4}$ alkyl), $NHC(O)(C_{1-4}$ alkyl), $NHS(O)_2$ ($C_{1-4}$ alkyl), $C(O)(C_{1-4}$ alkyl), $CF_3$ or $OCF_3$;
p and q are, independently, 0, 1 or 2;
$R^3$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, $R^{20}$, $R^{21}$ and $R^{22}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), C(O)N($C_{1-4}$ alkyl)$_2$ (and these alkyl groups optionally being joined to form a ring as described for $R^5$ and $R^6$ below), CO$_2$H, CO$_2$($C_{1-4}$ alkyl), NHC(O)($C_{1-4}$ alkyl), NHS(O)$_2$($C_{1-4}$ alkyl), C(O)($C_{1-4}$ alkyl), CF$_3$ or OCF$_3$) or heterocyclyl (optionally substituted by halogen, hydroxy, nitro, NH$_2$, NH($C_{1-4}$ alkyl), N($C_{1-4}$ alkyl)$_2$, S(O)$_2$($C_{1-4}$ alkyl), S(O)$_2$NH$_2$, S(O)$_2$NH($C_{1-4}$ alkyl), S(O)$_2$N($C_{1-4}$ alkyl)$_2$ (and these alkyl groups optionally being joined to form a ring as described for $R^5$ and $R^6$ below), cyano, $C_{1-4}$ alkyl, $C_{1-4}$ alkoxy, C(O)NH$_2$, C(O)NH($C_{1-4}$ alkyl), C(O)N($C_{1-4}$ alkyl)$_2$ (and these alkyl groups optionally being joined to form a ring as described for $R^5$ and $R^6$ below), CO$_2$H, CO$_2$($C_{1-4}$ alkyl), NHC(O)($C_{1-4}$ alkyl), NHS(O)$_2$($C_{1-4}$ alkyl), C(O)($C_{1-4}$ alkyl), CF$_3$ or OCF$_3$);

alternatively NR$^5$R$^6$, NR$^7$R$^8$, NR$^{12}$R$^{13}$, NR$^{14}$R$^{15}$, NR$^{18}$R$^{19}$, independently, form a 4-7 membered heterocyclic ring, azetidine, pyrrolidine, piperidine, azepine, 1,4-morpholine or 1,4-piperazine, the latter optionally substituted by $C_{1-4}$alkyl on the distal nitrogen;

$R^4$, $R^{17}$ and $R^{23}$ are, independently, $C_{1-6}$ alkyl (optionally substituted by halogen, hydroxy or $C_{3-10}$ cycloalkyl), CH$_2$($C_{2-6}$ alkenyl), phenyl (optionally substituted by halogen, hydroxy, nitro, NH$_2$, NH($C_{1-4}$ alkyl), N($C_{1-4}$ alkyl)$_2$ (and these alkyl groups optionally being joined to form a ring as described for $R^5$ and $R^6$ above), S(O)$_2$($C_{1-4}$ alkyl), S(O)$_2$NH$_2$, S(O)$_2$NH($C_{1-4}$ alkyl), S(O)$_2$N($C_{1-4}$ alkyl)$_2$ (and these alkyl groups optionally being joined to form a ring as described for $R^5$ and $R^6$ above), cyano, $C_{1-4}$ alkyl, $C_{1-4}$ alkoxy, C(O)NH$_2$, C(O)NH($C_{1-4}$ alkyl), C(O)N($C_{1-4}$ alkyl)$_2$ (and these alkyl groups optionally being joined to form a ring as described for $R^5$ and $R^6$ above), CO$_2$H, CO$_2$($C_{1-4}$alkyl), NHC(O)($C_{1-4}$ alkyl), NHS(O)$_2$($C_{1-4}$ alkyl), C(O)($C_{1-4}$ alkyl), CF$_3$ or OCF$_3$) or heterocyclyl (optionally substituted by halogen, hydroxy, nitro, NH$_2$, NH($C_{1-4}$ alkyl), N($C_{1-4}$ alkyl)$_2$ (and these alkyl groups optionally being joined to form a ring as described for $R^5$ and $R^6$ above), S(O)$_2$($C_{1-4}$ alkyl), S(O)$_2$NH$_2$, S(O)$_2$NH($C_{1-4}$ alkyl), S(O)$_2$N($C_{1-4}$ alkyl)$_2$ (and these alkyl groups optionally being joined to form a ring as described for $R^5$ and $R^6$ above), cyano, $C_{1-4}$ alkyl, $C_{1-4}$ alkoxy, C(O)NH$_2$, C(O)NH($C_{1-4}$ alkyl), C(O)N($C_{1-4}$ alkyl)$_2$ (and these alkyl groups optionally being joined to form a ring as described for $R^5$ and $R^6$ above), CO$_2$H, CO$_2$($C_{1-4}$ alkyl), NHC(O)($C_{1-4}$ alkyl), NHS(O)$_2$($C_{1-4}$ alkyl), C(O)($C_{1-4}$ alkyl), CF$_3$ or OCF$_3$);

$R^{24}$ is hydrogen, $C_{1-6}$ alkyl or benzyl;

or an N-oxide thereof; or a pharmaceutically acceptable salt thereof.

2. A compound of formula (I) as claimed in claim 1 wherein X is O.

3. A compound of formula (I) as claimed in claim 1 wherein $R^{24}$ is hydrogen.

4. A compound of formula (I) as claimed in claim 1 wherein $R^1$ is phenyl optionally substituted with fluorine, chlorine, $C_{1-4}$ alkyl or $C_{1-4}$ alkoxy.

5. A compound of formula (I) as claimed in claim 1 wherein $R^2$ is phenyl or heterocyclyl, either of which is optionally substituted by: halo, hydroxy, nitro, cyano, amino, $C_{1-4}$ alkyl (optionally substituted by S(O)$_2$($C_{1-4}$ alkyl) or S(O)$_2$phenyl), $C_{1-4}$ alkoxy, S(O)$_p$R$^4$ (wherein p is 0, 1 or 2), C(O)NH$_2$, NHS(O)$_2$($C_{1-4}$ alkyl), S(O)$_2$NH$_2$, S(O)$_2$NH($C_{1-4}$ alkyl) or S(O)$_2$N($C_{1-4}$ alkyl)$_2$; and $R^4$ is $C_{1-4}$ alkyl, $C_{1-4}$ hydroxyalkyl, $C_{3-7}$ cycloalkyl or $C_{3-7}$ cycloalkyl($C_{1-4}$ alkyl).

6. A process for preparing a compound of formula (I) as claimed in claim 1, the process comprising:

i. coupling a compound of formula (II):

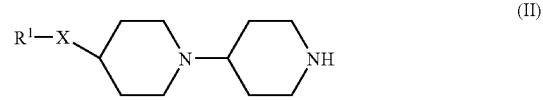

with a compound of formula (III):

wherein L is a suitable leaving group, in a suitable solvent; or, ii. reductive amination of a compound (II) with an ester compound of formula (IIIa):

in the presence of NaBH(OAc)$_3$ and acetic acid, followed optionally by removal of the ester group; or iii. a three component coupling of a compound of formula (II) with compounds of formula (IIIb) and (IIIc):

7. A pharmaceutical composition which comprises a compound of the formula (I), or a pharmaceutically acceptable salt thereof as claimed in claim 1, and a pharmaceutically acceptable adjuvant, diluent or carrier.

* * * * *

UNITED STATES PATENT AND TRADEMARK OFFICE
CERTIFICATE OF CORRECTION

PATENT NO. : 7,482,363 B2  
APPLICATION NO. : 10/508332  
DATED : January 27, 2009  
INVENTOR(S) : Hitesh Sanganee Page 1 of 1

It is certified that error appears in the above-identified patent and that said Letters Patent is hereby corrected as shown below:

Title Page, Column 1  
Lines 15 and 16, delete "This patent is subject to a terminal disclaimer."

Signed and Sealed this

Twenty-first Day of April, 2009

JOHN DOLL  
*Acting Director of the United States Patent and Trademark Office*

UNITED STATES PATENT AND TRADEMARK OFFICE
CERTIFICATE OF CORRECTION

PATENT NO. : 7,482,363 B2  Page 1 of 1
APPLICATION NO. : 10/508332
DATED : January 27, 2009
INVENTOR(S) : Sanganee et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 784 days Delete the phrase "by 784 days" and insert -- by 1053 days --

Signed and Sealed this

Twenty-second Day of June, 2010

David J. Kappos
*Director of the United States Patent and Trademark Office*